United States Patent
Luong-Van et al.

(10) Patent No.: US 8,969,648 B2
(45) Date of Patent: Mar. 3, 2015

(54) BLOOD CLOTTING SUBSTRATE AND MEDICAL DEVICE

(75) Inventors: Emma Kim Luong-Van, Singapore (SG); Isabel Rodriguez, Singapore (SG); Hong Yee Low, Botannia (SG); Audrey Yoke Yee Ho, Crescent (SG); Sriram Natarajan, Hillsborough, NJ (US); Noha Elmouelhi, Randolph, NJ (US); Kevin Cooper, Flemington, NJ (US); Murty Vyakarnam, Bridgewater, NJ (US); Chee Tiong Lim, Singapore (SG)

(73) Assignee: Ethicon, Inc., Somerville, NJ (US)

( * ) Notice: Subject to any disclaimer, the term of this patent is extended or adjusted under 35 U.S.C. 154(b) by 211 days.

(21) Appl. No.: 13/441,539

(22) Filed: Apr. 6, 2012

(65) Prior Publication Data
US 2013/0267880 A1     Oct. 10, 2013

(51) Int. Cl.
*A61F 13/00*     (2006.01)

(52) U.S. Cl.
USPC .................................. 602/43; 602/52; 602/58

(58) Field of Classification Search
CPC ..... A61F 13/00; A61F 13/02; A61F 13/0203; A61F 13/023; A61L 15/28; C08J 5/18; B31F 1/07; A61K 8/0208; A44B 18/0011
USPC ............ 602/41–43, 47–59; 428/99, 141, 156; 424/443
See application file for complete search history.

(56) References Cited

U.S. PATENT DOCUMENTS

| | | | |
|---|---|---|---|
| 4,256,693 A | 3/1981 | Kondo et al. | |
| 4,464,254 A | 8/1984 | Dojki et al. | |
| 4,557,264 A | 12/1985 | Hinsch | |
| 4,753,776 A | 6/1988 | Hillman et al. | |
| 4,911,165 A | 3/1990 | Lennard et al. | |
| 5,011,494 A | 4/1991 | von Recum et al. | |
| 5,176,692 A | 1/1993 | Wilk et al. | |
| 5,246,451 A | 9/1993 | Trescony et al. | |
| 5,246,666 A * | 9/1993 | Vogler et al. | 422/73 |
| 5,324,519 A | 6/1994 | Dunn et al. | |
| 5,344,611 A | 9/1994 | Vogler et al. | |
| 5,455,009 A | 10/1995 | Vogler et al. | |
| 5,569,272 A | 10/1996 | Reed et al. | |
| 5,723,219 A | 3/1998 | Kolluri et al. | |
| 6,267,772 B1 | 7/2001 | Mulhauser et al. | |
| 6,368,871 B1 | 4/2002 | Christel et al. | |
| 6,403,655 B1 | 6/2002 | Bezwada et al. | |
| 6,485,503 B2 | 11/2002 | Jacobs et al. | |
| 6,638,284 B1 | 10/2003 | Rousseau et al. | |
| 6,720,469 B1 | 4/2004 | Curtis et al. | |
| 6,872,439 B2 | 3/2005 | Fearing et al. | |

(Continued)

FOREIGN PATENT DOCUMENTS

DE     4126877 C1     11/1992
DE     19832634 A1    1/2000

(Continued)

OTHER PUBLICATIONS

U.S. Appl. No. 12/871,745, filed Aug. 30, 2010.

(Continued)

*Primary Examiner* — Kim M Lewis

(57) ABSTRACT

A blood clotting substrate and device which has a plurality of oxygen plasma-treated polypropylene pillars extending from the surface of a polypropylene film.

15 Claims, 2 Drawing Sheets

(56) References Cited

U.S. PATENT DOCUMENTS

| | | | |
|---|---|---|---|
| 6,913,697 B2 | 7/2005 | Lopez et al. | |
| 7,074,294 B2 | 7/2006 | Dubrow | |
| 7,195,872 B2 * | 3/2007 | Agrawal et al. | 435/287.2 |
| 7,331,199 B2 | 2/2008 | Ory et al. | |
| 7,479,318 B2 | 1/2009 | Jagota et al. | |
| 7,745,223 B2 | 6/2010 | Schubert et al. | |
| 7,754,233 B2 | 7/2010 | Andjelic et al. | |
| 7,988,733 B2 | 8/2011 | Shimp et al. | |
| 8,133,484 B2 | 3/2012 | Preiss-Bloom et al. | |
| 2003/0208888 A1 | 11/2003 | Fearing et al. | |
| 2004/0076822 A1 | 4/2004 | Jagota et al. | |
| 2004/0125266 A1 | 7/2004 | Miyauchi et al. | |
| 2005/0106552 A1 | 5/2005 | Ikeda | |
| 2005/0181629 A1 | 8/2005 | Jagota et al. | |
| 2006/0005362 A1 | 1/2006 | Arzt et al. | |
| 2006/0034734 A1 | 2/2006 | Schubert et al. | |
| 2006/0078724 A1 | 4/2006 | Bhushan et al. | |
| 2006/0154063 A1 | 7/2006 | Fujihara et al. | |
| 2006/0204738 A1 | 9/2006 | Dubrow et al. | |
| 2007/0227967 A1 | 10/2007 | Sakaino et al. | |
| 2007/0299542 A1 | 12/2007 | Mathisen et al. | |
| 2008/0124246 A1 | 5/2008 | Diaz-Quijada et al. | |
| 2008/0217180 A1 | 9/2008 | Doye et al. | |
| 2008/0241512 A1 | 10/2008 | Boris et al. | |
| 2008/0241926 A1 | 10/2008 | Lee et al. | |
| 2008/0280085 A1 | 11/2008 | Livne | |
| 2009/0130372 A1 | 5/2009 | Fukui et al. | |
| 2009/0318843 A1 | 12/2009 | Van Holten et al. | |
| 2010/0098909 A1 | 4/2010 | Reyssat et al. | |
| 2010/0137903 A1 | 6/2010 | Lee et al. | |
| 2011/0021965 A1 | 1/2011 | Karp et al. | |
| 2011/0160869 A1 | 6/2011 | Duch et al. | |
| 2011/0172760 A1 | 7/2011 | Anderson | |
| 2011/0177288 A1 | 7/2011 | Bhushan et al. | |
| 2011/0282444 A1 | 11/2011 | Liu et al. | |
| 2011/0293667 A1 | 12/2011 | Baksh et al. | |
| 2012/0052234 A1 * | 3/2012 | Natarajan et al. | 428/99 |
| 2012/0143228 A1 | 6/2012 | Natarajan et al. | |
| 2012/0251611 A1 | 10/2012 | Luong-Van et al. | |
| 2012/0302427 A1 | 11/2012 | Elmouelhi et al. | |
| 2012/0302465 A1 | 11/2012 | Elmouelhi et al. | |
| 2013/0172927 A1 | 7/2013 | Natarajan et al. | |
| 2013/0206330 A1 | 8/2013 | Natarajan et al. | |
| 2013/0266761 A1 | 10/2013 | Ho et al. | |
| 2013/0288225 A1 | 10/2013 | Elmouelhi et al. | |

FOREIGN PATENT DOCUMENTS

| | | |
|---|---|---|
| EP | 1416303 | 5/2004 |
| JP | 2004170935 A | 6/2004 |
| JP | 2013-226413 A | 11/2013 |
| SG | 193370 A | 10/2013 |
| WO | 0056808 | 9/2000 |
| WO | 03/099160 A1 | 12/2003 |
| WO | 2004/094303 A2 | 11/2004 |
| WO | 2006031197 | 3/2006 |
| WO | 2009/123739 A1 | 4/2008 |
| WO | 2009/067482 A1 | 5/2008 |
| WO | 2008/076390 A2 | 6/2008 |
| WO | 2008/102620 A1 | 8/2008 |
| WO | 2009022911 A2 | 2/2009 |
| WO | 2009029045 | 3/2009 |
| WO | 2009/067482 A1 | 5/2009 |
| WO | 2010/129641 A1 | 11/2010 |
| WO | 2011/026987 A1 | 3/2011 |
| WO | WO 2012/030570 A1 | 3/2012 |
| WO | WO 2012/162451 A2 | 11/2012 |
| WO | WO 2012/162452 A2 | 11/2012 |
| WO | WO 2013/102085 A1 | 7/2013 |
| WO | WO 2013/163304 A1 | 10/2013 |

OTHER PUBLICATIONS

U.S. Appl. No. 13/340,331, filed Dec. 29, 2011.
U.S. Appl. No. 13/340,405, filed Dec. 29, 2011.
U.S. Appl. No. 13/435,544, filed Mar. 30, 2012.
U.S. Appl. No. 13/441,496, filed Apr. 6, 2012.
U.S. Appl. No. 13/116,721, filed May 26, 2011.
U.S. Appl. No. 13/458,825, filed Apr. 27, 2012.
Sriram Natarajan, PCT No. PCT/US2011/048,584 Filed Aug. 22, 2011.
Emma Kim Luong-Van, U.S. Appl. No. 13/441,539, filed Apr. 6, 2012.
Definition of "Integral", Merriam-Webster Dictionary online, pp. 1-3, Accessed Oct. 15, 2013.
International Search report for International Application No. PCT/US2011/048584 dated Feb. 20, 2012.
International Search report for International Application No. PCT/US2012/072081 dated Mar. 12, 2013.
Sitti, "High Aspect Ratio Polymer Micro/Nano-Structure Manufacturing using Nanoembossing, Nanomolding and Directed Self-Assmbly", IEEE/ASME Advanced Mechatronics Conference, Kobe, Japan, Jul. 2003 (5 pages).
Tsougeni, et al. "Nano-texturing of poly (methyl methacrylate) polymer using plasma processes and applications in wetting control and protein adsorption", Microelectronic Engineering 86 (2009), pp. 1424-1427.
Vlachopoulou, et al., "Effect of surface nanostructuring of PDMS on wetting properties, hydrophobic recovery and protein adsorption", Microelectronic Engineering 86 (2009), pp. 1321-1324.
Gristina, "Biomaterial-Centered Infection: Microbial Adhesion Versus Tissue Integration", Science, vol. 237, Sep. 25, 1987, pp. 1588-1595.
Won, et al., "The Fabrication of Protein Nano Arrays Using 3-Dimensional Plastic Nanopillar Patterns", Journal of Nanoscience and Nanotechnology, 2011, vol. 11, pp. 4231-4235.
Zhao, et al., "Self-organized Polymer Aggregates with a Biomimetic Hierarchical Structure and its Superhydrophobic Effect", Cell Biochem Biophys (2007) 49: pp. 91-97.
Bhushan, et al. "Self-Cleaning Efficiency of Artificial Superhydrophobic Surfaces", Langmuir, 2009, 25, pp. 3240-3248.
Shi, et al., "Communication towards bioinspired superhydrophobic poly (L-lactic acid) surfaces using phase inversion-based methods", Bioinsp. Biomim. 3 (2008) (6 pages).
Jung, et al., "Wetting Behavior of Water and Oil Droplets in Three-Phase Interfaces for Hydrophobicity/philicity and Oleophobicity/philicity", Langmuir 2009, 25 (24), pp. 14165-14173.
Lee, et al., "Fabrication of Heirarchical Structures on a Polymer Surface to Mimic Natural Superhydrophobic Surfaces", Adv. Mater. 2007, 19, pp. 2330-2335.
Cha, et al., "Effect of Replicated Polymeric Substrate with Lotus Surface Structure on Adipose-Derived Stem Cell Behaviors", Macromol. Biosci. 2011, 11, pp. 1357-1363.
Yanagishita, et al., "Anti-Reflection Structures on Lenses by Nanoimprinting Using Ordered Anodic Porous Alumina", Applied Physics Express 2 (2009) (3 pages).
Schulte, et al., "Heirarchically structured superhydrophobic flowers with low hysteresis of the wild pansy (viola tricolor)—new design principals for biomimetic materials", Bellstein J. Nanotechnol. 2011, 2, pp. 228-236.
Bhushan, et al., "Micro-, nano- and Heirarchical structures for superhydrophobicity, self-cleaning and low adhesion", Phil. Trans. R. Soc. A. 2009, 367, pp. 1631-1672.
Occhiello, et al., "Oxygen-Plasma-Treated Polypropylene Interfaces with Air, Water, and Epoxy Resins: Part 1. Air and Water.", 1991, Journal of Applied Polymer Science, 42, pp. 551-559.
Gerard, et al., "Surface modifications of polypropylene membranes used for blood filtration", 2011, Polymer, 52, pp. 1223-1233.
Roure, et al., "Force Mapping in Epithelial Cell Migration", pp. 2390-2395, PNAS, Feb. 15, 2005, vol. 102, No. 7.
Oxford Dictionary Online Definition of "Cylinder", Oct. 15, 2013.
International Search Report for PCT/US2012/039256 dated Mar. 5, 2013.
Wan Y., et al., "Characterization of surface property of poly (lactide-co-glycolide) after oxygen plasma treatment", Biomaterials, Elsevier Science Publishers, vol. 25, No. 19, Aug. 1, 2004, pp. 4777-4783.
Jianhua Wei, et al., "Influence of surface wettability on competitive protein adsorption and initial attachment of osteoblasts; Competitive

(56) References Cited

OTHER PUBLICATIONS protein adsorption and initial cell attachment", Biomedical Materials, Institute of Physics Publishing, vol. 4, No. 4, Aug. 1, 2009, p. 45002.

Tsougeni K., et al., "Mechanisms of oxygen plasma nanotexturing of organic polymer surfaces: From stable super hydrophilic to super hydrophobic surfaces", Langmuir, American Chemical Society, vol. 25, No. 19, Oct. 6, 2009, pp. 11748-11759.

Messina G.M.L., et al., "A multitechnique study of preferential protein adsorption on hydrophobic and hydrophilic plasma-modified polymer surfaces", Colloids and Surfaces. B., Biointerfaces, vol. 70, No. 1, Apr. 1, 2009, pp. 76-83.

Chen H. et al., "The effect of surface microtopography of poly (dimethylsiloxane) on protein adsorption, platelet and cell adhesion", Colloids and Surfaces. B., Biointerfaces, vol. 71, No. 2, Jul. 1, 2009, pp. 275-281.

Saez et al., "Rigidity-driven growth and migration of epithelial cells on microstructured anisotropic substrates", PNAS, vol. 104, No. 20, pp. 8281-8286, May 15, 2007.

Sriram Natarajan, U.S. Appl. No. 12/871,745, filed Aug. 30, 2010.

Noha Elmouelhi, U.S. Appl. No. 13/116,721, filed May 26, 2011.

Sriram Natarajan, PCT No. PCT/US2011/048584 Filed Aug. 22, 2011.

Sriram Natarajan, U.S. Appl. No. 13/340,331, filed Dec. 29, 2011.

Noha Elmouelhi, U.S. Appl. No. 13/340,405, filed Dec. 29, 2011.

Emma Kim Luong-Van, U.S. Appl. No. 13/435,544, filed Mar. 30, 2012.

Audrey Yoke Yee Ho, U.S. Appl. No. 13/441,496, filed Apr. 6, 2012.

Noha Elmouelhi, U.S. Appl. No. 13/458,825, filed Apr. 27, 2012.

Noha Elmouelhi, PCT No. PCT/US2012/039256 filed May 12, 2012.

Sriram Natarajan, U.S. Appl. No. 13/730,259, filed Dec. 28, 2012.

Sriram Natarajan, PCT No. PCT/US2012/072081 filed Dec. 28, 2012.

Sriram Natarajan, U.S. Appl. No. 13/841,561, filed Mar. 15, 2013.

Noha Elmouelhi, PCT No. PCT/US2013/038007 filed Apr. 24, 2013.

Audrey Yoke Yee Ho, U.S. Appl. No. 14/139,673, filed Dec. 23, 2013.

S.D. Lee, "Surface Modification of Polypropylene Under Argon and Oxygen-RF-Plasma Conditions", Plasmas and Polymers, vol. 2, No. 3, Sep. 1, 1997, pp. 177-198.

International Search Report for PCT/US2013/038007 dated Jun. 18, 2013.

\* cited by examiner

BLOOD CLOTTING SUBSTRATE AND MEDICAL DEVICE

FIELD OF THE INVENTION

The present invention relates to polymeric blood clotting substrates.

BACKGROUND OF THE INVENTION

There is an ongoing need for blood clotting substrates having improved blood clotting activity. Such structures can be suited to use in various applications, such as medical applications, surgical applications and the like, or wherever and whenever reduction of blood clotting time is desired.

Many blood clotting substrates are currently commercially available. Hemostatic bandages incorporating fibrinogen and/or thrombin, both natural products, are available. However, these naturally-derived products can be expensive to obtain and prepare for use in hemostatic substrates, since they require isolation from their source materials, formation into suitable substrate forms and subsequent sterilization. Likewise, hemostatic bandages exist which incorporate various additives, such as zeolite crystals or chitosan, as hemostasis enhancers. Again, preparation of these substrates can be expensive due to the complicated processes necessary to stably incorporate these solid powder materials into the substrate.

U.S. Pat. No. 8,133,484 discloses an adhesive material comprising gelatin and a non-toxic cross-linking material such as transglutaminase. The adhesive material is useful for medical purposes as hemostatic products. The hemostatic products are useful for the treatment of wounded tissue. The background section of this patent provides a detailed history of hemostatic devices.

It would be desirable to develop a blood clotting substrate having a comparatively simple design which could be made from relatively inexpensive synthetic materials, and has adequate surface characteristics to enhance blood clotting without incorporation of extraneous materials.

U.S. Pat. No. 7,745,223 discloses a method to increase the adhesion strength of coagulated blood on a surface by increasing the surface interaction of blood-inherent components like fibrin/fibrinogen and thrombocytes by treating the surface by exposing it to ionized atoms or molecules. The surface treatment according to the invention is applied on plastic disposables used in blood diagnostics (e.g. hemostasis analysis) as well as medical implants like artery sealings. The improved blood clot adhesion results in higher diagnostic security due to reduced measurement failure (e.g., for patients with increased thrombocyte content) and in better significance of special tests (e.g., hyperfibrinolysis diagnosis).

U.S. Pat. Nos. 5,344,611 and 5,455,009 describe processes for reducing hemostasis time in blood collection devices by plasma-treating an inside wall surface of a polymeric blood collection tube, or by inserting a plasma-treated plastic insert into such a collection tube. However, U.S. Pat. No. 5,344,611 discloses that not all plasma-treated plastics demonstrate improved clotting times.

The present inventors have discovered an integrally formed substrate, made from a single synthetic polymer, which acts to enhance blood clotting, without incorporation of dissimilar powders or foams.

SUMMARY OF THE INVENTION

The present invention relates to a blood clotting substrate, comprising a plurality of oxygen plasma-treated polypropylene pillars extending from the surface of a polypropylene film.

In another embodiment, the present invention is directed to a method of blood clotting, comprising contacting blood with a blood clotting substrate, comprising a plurality of oxygen plasma-treated polypropylene pillars extending from the surface of a polypropylene film.

In another embodiment, the present invention is directed to a method of promoting blood clotting, comprising contacting blood with a blood clotting medical device, comprising a substrate and a polypropylene film having a plurality of oxygen plasma-treated polypropylene pillars extending from the surface thereof.

In another embodiment, the invention is directed to a method of forming a blood clotting substrate, comprising a) providing a specific solvent-dissolvable mold including indentations; b) providing a polypropylene film to the mold under conditions sufficient to permit filling the indentations of the mold by the polypropylene; c) treating the mold and polypropylene of step b) to an extent sufficient to substantially solidify the polypropylene; d) exposing the mold and polypropylene to the specific solvent (selected to dissolve the mold but not the polypropylene) under mold-dissolving conditions to provide a pillared substrate; and e) oxygen plasma-treating the pillared substrate.

DETAILED DESCRIPTION

The invention is directed to a polypropylene film having integral, high aspect ratio (HAR), length to diameter polypropylene (PP) sub-micron to micron-sized densely packed pillared surface features on the film, that when further oxygen plasma-treated to increase wettability, will enhance blood clotting.

In one embodiment, the pillars have an average diameter ranging from 0.2 to 5 microns, preferably from about 0.8 μm to about 3 μm, and aspect ratios (length/diameter) of from about 0.5 to about 40, preferably from about 2 to about 25. In a particularly preferred embodiment, the pillars have a diameter of about 1 μm and a height of about 20 μm.

The surfaces of the polypropylene films/pillars are treated by oxygen plasma treatment using a microwave plasma processor (100 W, 30 seconds). Oxygen plasma treatment results in the polypropylene film and pillars having a higher oxygen content on the surface thereof as compared to non-oxygen plasma-treated polypropylene film and pillars. Depending on the severity of the treatment, the polypropylene film and pillars can have an oxygen content of about 21%.

It has been determined that the oxygen-plasma treated films and pillars result in a substrate having static water contact angles of less than about 15°, such that the substrate demonstrates super-hydrophilicity, even though polypropylene is well-known to be highly hydrophobic.

Figure 2:
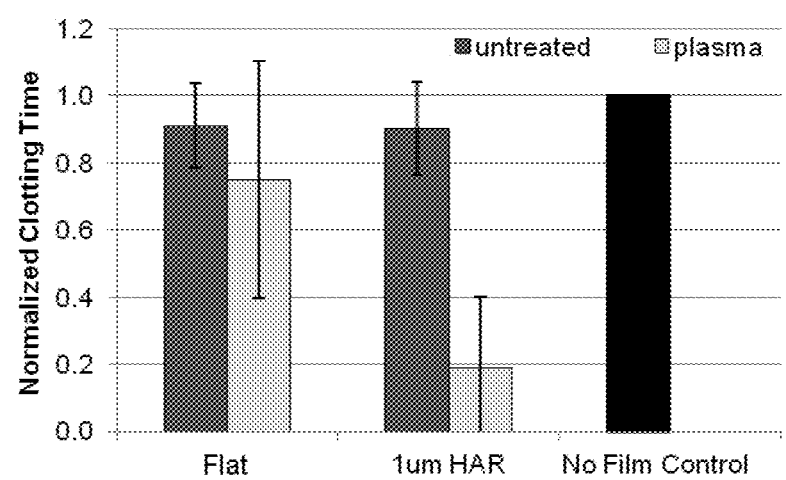
FIG. 2 is a graph comparing normalized blood clotting times of untreated and oxygen plasma-treated polypropylene surfaces.

Advantageously, as shown in the graph in FIG. 2, the oxygen plasma-treated polypropylene film with the protruding surface pillars demonstrates a clotting time of 0.2, normalized to a no-film control clot time of 0.9.

In yet still another embodiment, the blood clotting substrate surface is substantially planar and the pillars are within about ±45 degrees of normal to the planar surface, more preferably within about ±30 degrees of normal to the planar surface.

In another embodiment, the blood clotting substrate has a pillar density of from $1 \times 10^5$ to $6 \times 10^8$ pillars/cm$^2$. For present purposes, "pillar density" can be described as the number of pillars or pillars present per square centimeter of adhesive structure surface.

In still another embodiment, the blood clotting substrate has a density of pillars on its surface ranging from about $1 \times 10^7$ to about $5 \times 10^7$ pillars per cm$^2$.

In another embodiment, the invention is directed to a blood clotting medical device, comprising a substrate and a polypropylene film having a plurality of oxygen plasma-treated polypropylene pillars extending from the surface thereof.

The surfaces of the polypropylene films/pillars of the device are treated by oxygen plasma treatment using a microwave plasma processor (100 W, 30 seconds). Oxygen plasma treatment results in the polypropylene film and pillars having a higher oxygen content on the surface thereof as compared to non-oxygen plasma-treated polypropylene film and pillars. Depending on the severity of the treatment, the polypropylene film and pillars can have an oxygen content of about 21%.

In a preferred embodiment, the polypropylene film of the blood clotting medical device is oxygen plasma-treated, and the pillars are of a diameter from about 0.8 μm to about 3 μm and have an aspect ratio from about 0.5 to about 40, preferably from about 2 to about 25. In a preferred embodiment, the pillars have a diameter of about 1 μm and a height of about 20 μm.

It has been determined that the oxygen-plasma treated films and pillars result in a blood clotting medical device having static water contact angles of less than about 15°, such that the device demonstrates super-hydrophilicity, even though polypropylene is well-known to be highly hydrophobic. The blood clotting medical device demonstrates clotting times of 0.2, normalized to an untreated film clot time of 0.9.

Another embodiment of the invention is directed to a method of promoting blood clotting, comprising contacting blood with a blood clotting substrate, comprising a plurality of oxygen plasma-treated polypropylene pillars extending from the surface of a polypropylene film.

Alternatively, the invention is directed to a method of promoting blood clotting, comprising contacting blood with a blood clotting medical device, comprising a polypropylene film having a plurality of oxygen plasma-treated polypropylene pillars extending from the surface thereof.

In another embodiment, the blood clotting substrate is at least partially formed by a process selected from nano- or micro-molding using a template, polymer self-assembly, lithography, and etching. For example, a method of forming the blood clotting substrate comprises a) providing a specific solvent-dissolvable mold including indentations; b) providing a polypropylene film to the mold under conditions sufficient to permit filling the indentations of the mold by the polypropylene; c) treating the mold and polypropylene of step b) to an extent sufficient to substantially solidify the polypropylene; d) exposing the mold and polypropylene the specific solvent (selected to dissolve the mold but not the polypropylene) under mold-dissolving conditions to provide a pillared substrate; and e) oxygen plasma-treating the pillared substrate.

The invention is further explained in the description that follows with reference to the drawings illustrating, by way of non-limiting examples, various embodiments of the invention.

EXAMPLE 1

This example shows that polypropylene densely-packed surface structures of high aspect ratio can be oxygen plasma-treated to yield higher surface area and higher oxygen content on the surface and thus result in faster whole blood clotting times. Polypropylene pillars of diameter 1 micron and height 20 micron were fabricated using a polycarbonate membrane as a mold and an imprinting process as follows:

A commercial track-etched polycarbonate membrane was obtained from Millipore Corporation of Billerica, Mass., USA of having pores of 1 micron diameter and a circular diameter of 2.5 cm, with a thickness of 20 micron.

The membrane was used as a template to imprint a solvent-resistant polypropylene polymer film of 300 micron thickness, obtained from Ethicon, Inc. of Somerville, N.J., USA. The polypropylene film was pressed into the polycarbonate membrane template under high temperature and pressures (180° C., 600 kPa (6 bar)) for 20 minutes, melting the polypropylene.

The polypropylene polymer and the membrane are cooled to 175° C. before removal of pressure, after which the polymer structures are de-molded and released by dissolving the membrane in dichloromethane.

Some films were oxygen plasma-treated using a microwave plasma processor at 100 W for 30 seconds.

The porous solvent-dissolvable polycarbonate material which acts as a template for the pillar-like pillars of the product can be substituted by another solvent-dissolvable porous polymeric material. Alternately, a strippable mold such as anodized aluminum oxide can be substituted to provide the pillar-like cylindrical pillars of the final product, without the need for exposure to a chemical solvent. Polyimide film (sold under the tradename KAPTON™ by E.I. du Pont de Nemours and Company, Wilmington, Del.) was used as a capping means or shield to protect polymer surfaces from directly contacting surfaces such as metal. Other suitable substantially chemically inert materials which can also be provided as a film or other layer for this purpose include polytetrafluoroethylene (sold under the tradename TEFLON™ by E.I. du Pont de Nemours and Company, Wilmington, Del.). Advantageously, these materials are not reactive with the polycarbonate solvent-dissolvable mold or template material and can be readily removed or peeled therefrom once compression is completed.

Figure 1:
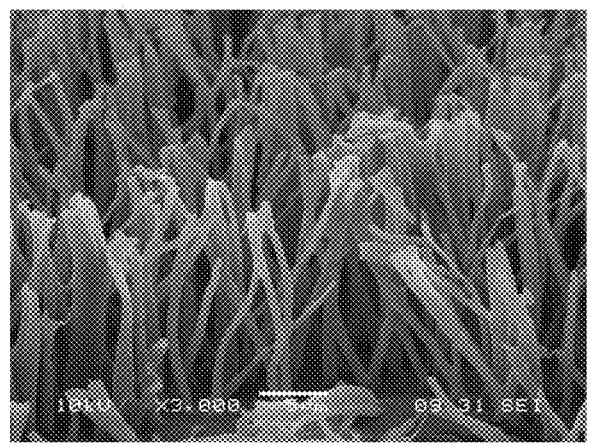
FIG. 1 is a scanning electron microscope image of a polypropylene substrate showing the polypropylene high surface area pillars.

The surface area ratio for these structures is 6.5 times the surface area of a flat film as shown by FIG. 1 which depicts an SEM image showing the polypropylene high surface area pillars.

Static water contact angle measurements, herein referred to as contact angle measurements, were conducted using a sessile drop method. A Rame-Hart contact angle goniometer with Drop Image software was used. Plasma treatment was done immediately before contact angle measurement. Two microliter drops of de-ionized water were placed on the surface for measurement, and 5 measurements were taken for each surface. The mean contact angle is reported in Table 1, below.

TABLE 1

| | PP Water Contact Angles | |
| --- | --- | --- |
| | Untreated | Treated |
| Flat | 101° | 59° |
| Pillars | 148° | 14° |

The contact angle of the untreated pillared structures is higher than the corresponding flat film (148° vs 101°), implying their greater hydrophobicity or non-wettability. Oxygen plasma treatment greatly reduces the contact angle for water on these surfaces, as shown in Table 1, resulting in wettable surfaces (and greater hydrophilicity).

Surface elemental analysis was conducted on flat films with results shown in Table 2, below. The oxygen plasma treatment results in a higher oxygen content on the film (20.9% versus 4.3%).

TABLE 2

| Element | Untreated PP | Plasma-treated PP |
| --- | --- | --- |
| C | 95.7% | 79.1% |
| O | 4.3% | 20.9% |

Flat films and high aspect ratio structured films, both untreated and oxygen-plasma treated, were evaluated for in vitro whole blood clot times. Rabbit blood was collected from a New Zealand white rabbit in EDTA tubes (BD Biosciences). Blood was stored at 4° C. and used within 2 days of collection. Films were incubated in a 24-well plate (Nunc) with 300 microliter room temperature EDTA anti-coagulated rabbit whole blood. 50 microliter of 0.1 M calcium chloride (GCE Laboratory Chemicals) was added to initiate coagulation, and the samples were gently rocked. Time to clotting was observed and recorded. A control test without film in one of the wells (no-film control) was run at the same time. The clotting time of the no-film control was approx. 20 minutes. The clot time of the test samples was normalized to the no-film control clot time (FIG. 2). The 1 um high aspect ratio pillar films with oxygen plasma treatment show the fastest clotting times with a normalized clot time of 0.2 versus the untreated film clot time of 0.9. Plasma treatment alone or high aspect ratio pillars alone do not result in such a fast clot time.

EXAMPLE 2 (COMPARATIVE)

Figure 3:
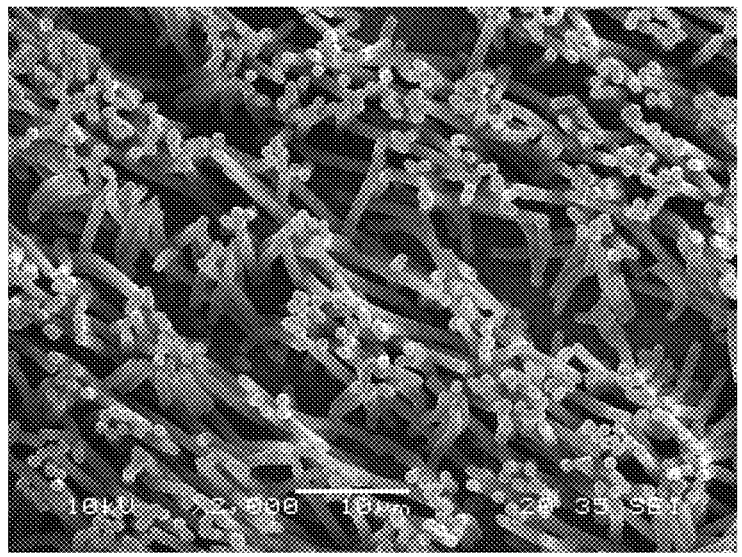
FIG. 3 is a scanning electron microscope image of a polydioxanone substrate showing the polydioxanone high surface area pillars.

High aspect ratio pillars were fabricated using polydioxanone (PDO) films in a similar method as described in Example 1. An SEM image of the 1 um diameter pillars with 20 um height (aspect ratio 20) are shown in FIG. 3. Static water contact angle measurements were conducted as outlined in Example 1. The mean contact angle is reported in Table 3, below.

TABLE 3

| | PDO Water Contact Angles | |
| --- | --- | --- |
| | Untreated | Treated |
| Flat | 80° | 14° |
| Pillars | <10° | <10° |

The contact angle of the pillared structures was lower than the corresponding flat film (<10° vs 80°), even in the absence of oxygen plasma treatment.

Surface elemental analysis was conducted on flat PDO films as outlined in Example 1. The untreated and oxygen plasma-treated both have similar oxygen content, as shown in Table 4.

TABLE 4

| Element | Untreated PDO | Plasma-treated PDO |
| --- | --- | --- |
| C | 55.5% | 54.4% |
| O | 38.1% | 42.1% |

Figure 4:
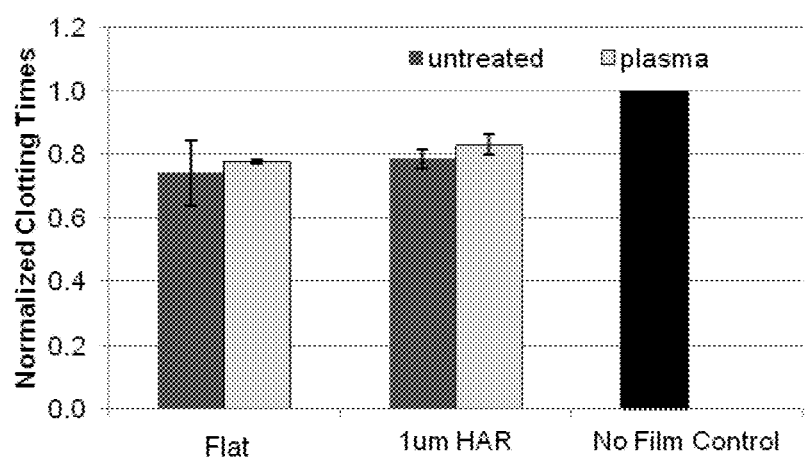
FIG. 4 is a graph comparing normalized blood clotting times of untreated and oxygen plasma-treated polydioxanone surfaces.

Flat PDO films and high aspect ratio structured PDO films, both untreated and oxygen plasma-treated, were evaluated for in vitro whole blood clot times. All clot times were normalized to the no-film control, and are shown in FIG. 4. Unlike the polypropylene samples, no reduction in clot times was observed for the untreated polydioxanone structures and/or the oxygen plasma treated structures. All of the samples exhibited similar clot times.

All patents, test procedures, and other documents cited herein, including priority documents, are fully incorporated by reference to the extent such disclosure is not inconsistent and for all jurisdictions in which such incorporation is permitted.

When numerical lower limits and numerical upper limits are listed herein, ranges from any lower limit to any upper limit are contemplated.

The invention being thus described, it will be apparent that the same may be varied in many ways. Such variations are not to be regarded as a departure from the spirit and scope of the invention, and all such modifications as would be obvious to one skilled in the art are intended to be included within the scope of the following claims.

What is claimed:

1. A method of promoting blood clotting, comprising contacting blood with a blood clotting substrate comprising a plurality of oxygen plasma-treated polypropylene pillars extending from a surface of a oxygen plasma-treated polypropylene film, wherein the film and pillars demonstrate a normalized clotting time of 0.2, compared to an untreated film clot time of 0.9 when contacted with blood.

2. A method of promoting blood clotting, comprising contacting blood with a blood clotting medical device, comprising an oxygen plasma-treated polypropylene film having a plurality of oxygen plasma-treated polypropylene pillars extending from a surface thereof, wherein the oxygen plasma-treated polypropylene film and pillars demonstrate a normalized clotting time of 0.2, compared to an untreated film clot time of 0.9 when contacted with blood.

3. A method of forming a blood clotting substrate, comprising:
  a) providing a mold dissolvable by a specific solvent including indentations;
  b) providing a polypropylene film to the mold under conditions sufficient to permit filling the indentations of the mold by the polypropylene;
  c) treating the mold and polypropylene of step b) to an extent sufficient to substantially solidify the polypropylene;
  d) exposing the mold and polypropylene to the specific solvent selected to dissolve the mold but not the polypropylene under mold-dissolving conditions to provide a pillared substrate; and
  e) oxygen plasma-treating the pillared substrate.

4. A blood clotting substrate, comprising a plurality of polypropylene pillars extending from a surface of a polypropylene film, wherein the polypropylene pillars and polypropylene film have been oxygen plasma-treated and demonstrate a normalized clotting time of 0.2, compared to an untreated film clot time of 0.9 when contacted with blood.

5. The blood clotting substrate of claim 4, wherein the pillars are of a diameter from about 0.8 μm to about 3 μm and have aspect ratios from about 0.5 to about 40.

6. The blood clotting substrate of claim 5, wherein the pillars have a diameter of about 1 μm and a height of about 20 μm.

7. The blood clotting substrate of claim 4, which has a static water contact angle of less than about 15°.

8. The blood clotting substrate of claim 4, wherein the polypropylene film and pillars have a higher oxygen content on surfaces thereof than non-oxygen plasma treated polypropylene film and pillars.

9. The blood clotting substrate of claim 4, wherein the polypropylene film and pillars have an oxygen content of about 21%.

10. A blood clotting medical device, comprising an oxygen plasma-treated polypropylene film having a plurality of oxygen plasma-treated polypropylene pillars extending from a surface thereof, wherein the oxygen plasma-treated polypropylene film and pillars demonstrate a clotting time of 0.2, normalized to an untreated film clot time of 0.9 when contacted with blood.

11. The blood clotting medical device of claim 10, wherein the pillars are of a diameter from about 0.8 μm to about 3 μm and have aspect ratios from about 0.5 to about 40.

12. The blood clotting medical device of claim 11, wherein the pillars have a diameter of about 1 μm and a height of about 20 μm.

13. The blood clotting medical device of claim 10, which has a static water contact angle of less than about 15°.

14. The blood clotting medical device of claim 10, wherein the polypropylene film and pillars have a higher oxygen content on surfaces thereof than non-oxygen plasma treated polypropylene film and pillars.

15. The blood clotting medical device of claim 10, wherein the polypropylene film and pillars have an oxygen content of about 21%.

* * * * *